(12) United States Patent
Eppstein et al.

(10) Patent No.: US 6,730,028 B2
(45) Date of Patent: May 4, 2004

(54) CONTROLLED REMOVAL OF BIOLOGICAL MEMBRANE BY PYROTECHNIC CHARGE FOR TRANSMEMBRANE TRANSPORT

(75) Inventors: Jonathan A. Eppstein, Atlanta, GA (US); Michael R. Hatch, Sugar Hill, GA (US); Joseph Papp, Duluth, GA (US); Mark L. Faupel, Alpharetta, GA (US); Krishna Kumar, Duluth, GA (US)

(73) Assignee: Altea Therapeutics Corporation, Tucker, GA (US)

( * ) Notice: Subject to any disclaimer, the term of this patent is extended or adjusted under 35 U.S.C. 154(b) by 200 days.

(21) Appl. No.: 10/040,066

(22) Filed: Oct. 29, 2001

(65) Prior Publication Data

US 2002/0091311 A1 Jul. 11, 2002

Related U.S. Application Data

(62) Division of application No. 09/353,130, filed on Jul. 14, 1999, now Pat. No. 6,352,506.
(60) Provisional application No. 60/092,731, filed on Jul. 14, 1998, and provisional application No. 60/138,050, filed on Jun. 8, 1999.

(51) Int. Cl.⁷ .............................. A61B 5/00; F42C 19/00; F42B 4/00
(52) U.S. Cl. .................. 600/309; 604/20; 606/131; 102/201; 102/335
(58) Field of Search .................. 600/309, 310, 600/316, 365, 573; 604/19, 20, 22, 49, 289, 290; 606/9, 131; 607/96, 100; 102/200, 201, 202.2, 202.5, 206, 335, 358

(56) References Cited

U.S. PATENT DOCUMENTS

| | | | |
|---|---|---|---|
| 5,224,928 A | 7/1993 | Sibalis et al. | |
| 5,249,095 A | * 9/1993 | Hunter | 102/202.5 |
| 5,380,272 A | 1/1995 | Gross | |
| 5,423,803 A | 6/1995 | Tankovich et al. | |
| 5,651,768 A | 7/1997 | Sibalis | |
| 5,713,845 A | 2/1998 | Tankovich | |
| 5,722,397 A | 3/1998 | Eppstein | |
| 5,752,949 A | 5/1998 | Tankovich et al. | |
| 5,817,089 A | 10/1998 | Tankovich et al. | |
| 5,847,309 A | * 12/1998 | Baginski | 102/202.2 |
| 5,885,211 A | 3/1999 | Eppstein et al. | |
| 5,925,035 A | 7/1999 | Tankovich | |
| 6,022,316 A | 2/2000 | Eppstein et al. | |
| 6,056,738 A | 5/2000 | Marchitto et al. | |
| 6,173,202 B1 | 1/2001 | Eppstein | |
| 6,247,485 B1 | 6/2001 | Rossi et al. | |
| 6,352,506 B1 | 3/2002 | Eppstein et al. | |

FOREIGN PATENT DOCUMENTS

| | | |
|---|---|---|
| WO | WO 96/41657 | 12/1996 |
| WO | WO 97/07734 | 3/1997 |
| WO | WO 98/00193 | 1/1998 |
| WO | WO 98/22719 | 5/1998 |
| WO | WO 98/29134 | 7/1998 |
| WO | WO 98/42267 | 10/1998 |
| WO | WO 99/29364 | 6/1999 |
| WO | WO 99/44507 | 9/1999 |
| WO | WO 99/44508 | 9/1999 |
| WO | WO 99/44637 | 9/1999 |
| WO | WO 99/44638 | 9/1999 |
| WO | WO 99/44678 | 9/1999 |
| WO | WO 00/03758 | 1/2000 |
| WO | WO 00/27473 | 5/2000 |
| WO | WO 00/74767 | 12/2000 |

* cited by examiner

Primary Examiner—Eric F. Winakur
(74) Attorney, Agent, or Firm—Nath & Associates PLLC; Gary M. Nath; Jerald L. Meyer

(57) ABSTRACT

A method and device for forming artificial openings in a biological membrane with a pyrotechnic charge that is exploded in a controlled manner in proximity of the biological membrane to form the artificial opening(s) therein. The method and device are useful in connection with transdermal delivery and monitoring applications.

26 Claims, 9 Drawing Sheets

CONTROLLED REMOVAL OF BIOLOGICAL MEMBRANE BY PYROTECHNIC CHARGE FOR TRANSMEMBRANE TRANSPORT

This application is a division of U.S. patent application Ser. No. 09/353,130, filed Jul. 14, 1999, now U.S. Pat. No. 6,352,506. which claims the benefit of priority to U.S. Provisional Patent Application No. 60/092,731, filed Jul. 14, 1998 and to U.S. Provisional Patent Application No. 60/138, 050 filed Jun. 8, 1999, the disclosures of each of which are incorporated herein by reference.

BACKGROUND OF THE INVENTION

This invention relates to transporting substances across a biological membrane of an animal, such as a human, and particularly to a device and method for forming openings in the biological membrane for delivering substances into the animal through the biological membrane for treatment applications or extracting sub stances from the animal through the biological membrane for monitoring or other diagnosis applications.

There are many techniques known in the art for making openings or holes in biological membranes, such as skin, for drug delivery and monitoring applications. One well known example of the need in the art for less painful puncturing of a biological membrane is in the field of diabetes monitoring. Diabetes patients often must submit to painful finger sticks, sometimes several times a day, with lancets and micro-lancets in order to obtain an adequate quantity of fluid. Other than the relative size of the lancets decreasing, the use of lancets, and the resulting finger sensitivity and pain, has not changed for many years. Other techniques have been developed, such as the use of laser, hydraulic jets, or electroporation, with the purpose of minimizing the pain and invasiveness of the procedure. See, for example, commonly assigned U.S. Pat. No. 5,885,211 to Eppstein et al, which is directed to thermal microporation techniques and devices to form one or more micropores in a biological membrane.

Each of these technologies have their associated advantages and disadvantages, and accordingly, other techniques are being developed that may prove to have broad application in all transmembrane transport applications.

SUMMARY

Briefly, the present invention is directed to a method and apparatus for forming artificial openings in a selected area of a biological membrane using a pyrotechnic element that is triggered to explode in a controlled fashion so that the micro-explosion produces the artificial opening in the biological membrane to a desired depth and diameter. The method and apparatus of the present invention is suitable for use in connection with analyte monitoring whereby access to a biological fluid is gained through the at least one opening. Likewise, this technique is useful for transmembrane delivery applications where it is desirable to delivery substances through the membrane into the organism.

The above and other objects and advantages of the present invention will become more readily apparent when reference is made to the following description taken in conjunction with the accompanying drawings.

DETAILED DESCRIPTION OF THE INVENTION

Figure 1:
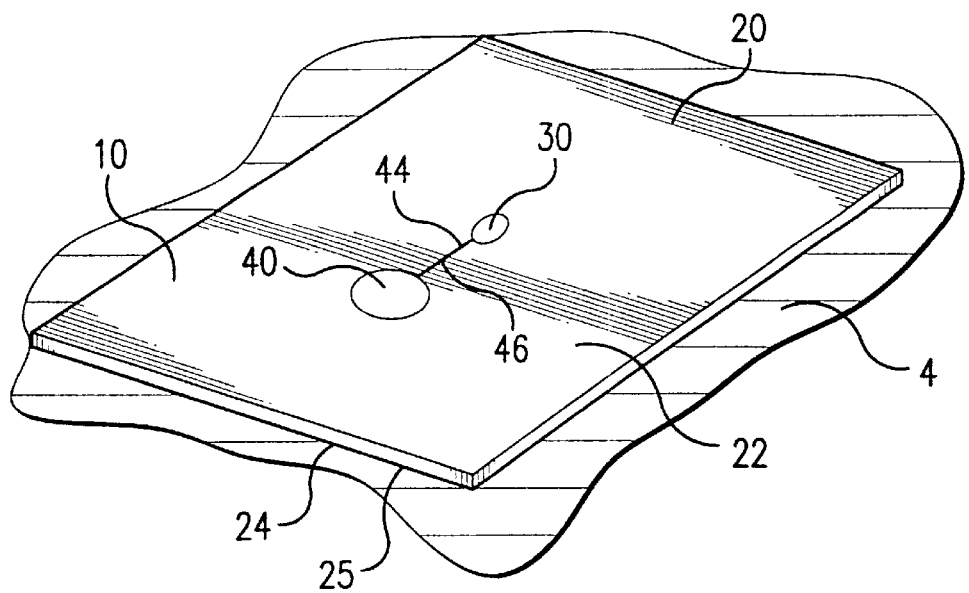
FIG. 1 is a perspective view of a device comprising a pyrotechnic element connected to a trigger element disposed on a substrate that is placed in proximity with a biological membrane of an organism.

It is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It is noted that, as used in this specification and the appended claims, the singular forms "a," "an," and "the" include plural referents unless the context clearly dictates otherwise. In describing and claiming the present invention, the following terminology will be used in accordance with the definitions set out below.

As used herein, the term "tissue" means an aggregate of cells of a particular kind, together with their intercellular substance, that forms a structural material. At least one surface of the tissue must be available for the present invention to be carried out. The preferred surface of the tissue is the skin.

As used herein, "poration," "microporation," or any such similar term means the formation of a small hole or pore in or through the biological membrane, such as skin or mucous membrane, or the outer layer of an organism to lessen the barrier properties of this biological membrane the passage of biological fluids, such as analytes from below the biological membrane for analysis or the passage of active permeants or drugs from without the biological membrane for selected purposes. Preferably the hole or "micropore" so formed is approximately 1-1000 μm in diameter and will extend into the biological membrane sufficiently to break the barrier properties of this layer without adversely affecting the underlying tissues. It is to be understood that the term "micropore" is used in the singular form for simplicity, but that the device of the present invention may form multiple artificial openings.

As used herein "penetration" means the controlled removal of cells caused by the thermal and kinetic energy released when the pyrotechnic element explodes which causes cells of the biological membrane and possibly some adjacent cells to be "blown away" from the site.

As used herein, "penetration enhancement" or "permeation enhancement" means an increase in the permeability of the biological membrane to a drug, analyte, or other chemical molecule, compound or particle (also called "permeant"), i.e., so as to increase the rate at which a drug, analyte, or other chemical molecule, compound or particle permeates the biological membrane and facilitates the increase of flux across the biological membrane for the purpose of the withdrawal of analytes out through the biological membrane or the delivery of drugs across the biological membrane and into the underlying tissues.

As used herein, "enhancer", "chemical enhancer," "penetration enhancer," "permeation enhancer," and the like includes all enhancers that increase the flux of a permeant, analyte, or other molecule across the biological membrane, and is limited only by functionality. In other words, all cell envelope disordering compounds and solvents and any other chemical enhancement agents are intended to be included. Additionally, all active force enhancer technologies such as the application of sonic energy, mechanical suction, pressure, or local deformation of the tissues, iontophoresis or electroporation are included. For example, ammonia may be used as an enhancer for the device of the present invention. In this example, the ammonia may increase the permeability of selected tissue structures, such as the capillary walls, within the tissues proximate to, or extending some distance from, the formed micropore. One or more enhancer technologies may be combined sequentially or simultaneously. For example, the ammonia enhancer may first be applied to permealize the capillary walls and then an iontophoretic or sonic energy field may be applied to actively drive a permeant into those tissues surrounding and comprising the capillary bed. The shock wave generated by the detonation of the pyrotechnic element of the present invention is itself a sonic permeation enhancer.

As used herein, "transdermal" or "percutaneous" means passage of a permeant into and through the biological membrane to achieve effective therapeutic blood levels or local tissue levels of a permeant, or the passage of a molecule or fluid present in the body ("analyte") out through the biological membrane so that the analyte molecule may be collected on the outside of the body.

As used herein, the term "permeant," "drug," or "pharmacologically active agent" or any other similar term means any chemical or biological material or compound suitable for transdermal administration by the methods previously known in the art and/or by the methods taught in the present invention, that induces a desired biological or pharmacological effect, which may include but is not limited to (1) having a prophylactic effect on the organism and preventing an undesired biological effect such as an infection, (2) alleviating a condition caused by a disease, for example, alleviating pain or inflammation caused as a result of disease, and/or (3) either alleviating, reducing, or completely eliminating the disease from the organism. The effect may be local, such as providing for a local anesthetic effect, or it may be systemic. Such substances include broad classes of compounds normally delivered into the body, including through body surfaces and membranes, including skin. In general, this includes but is not limited to: antiinfectives such as antibiotics and antiviral agents; analgesics and analgesic combinations; anorexics; antihelminthics; antiarthritics; antiasthmatic agents; anticonvulsants; antidepressants; antidiabetic agents; antidiarrheals; antihistamines; antiinflammatory agents; antimigraine preparations; antinauseants; antineoplastics; antiparkinsonism drugs; antipruritics; antipsychotics; antipyretics; antispasmodics; anticholinergics; sympathomimetics; xanthine derivatives; cardiovascular preparations including potassium and calcium channel blockers, beta-blockers, alpha-blockers, and antiarrhythmics; antihypertensives; diuretics and antidiuretics; vasodilators including general coronary, peripheral and cerebral; central nervous system stimulants; vasoconstrictors; cough, and cold preparations, including decongestants; hormones such as estradiol and other steroids, including corticosteroids; hypnotics; immunosuppressives; muscle relaxants; parasympatholytics; psychostimulants; sedatives; and tranquilizers. By the method of the present invention, both ionized and nonionized drugs may be delivered, as can drugs of either high or low molecular weight. Additionally, microparticles, DNA, RNA, viral antigens or any combination of the permeants listed above may be deliver by the present invention.

As used herein, an "effective" amount of a pharmacologically active agent means a sufficient amount of a compound to provide the desired local or systemic effect and performance at a reasonable benefit/risk ratio attending any medical treatment. An "effective" amount of a permeation or chemical enhancer as used herein means an amount selected so as to provide the desired increase in biological membrane permeability, the desired depth of penetration, rate of administration, and amount of drug delivered.

As used herein, a "pyrotechnic element" means any chemical, matter or combination of chemicals and/or matters that have an explosive characteristic when suitably detonated. The pyrotechnic element of the present invention undergoes very rapid decomposition (as combustion) with the production of heat and the formation of more stable materials (as gases) which exert pressure as they expand at the high temperature produced thereby creating a shock wave with a high peak pressure lasting for a short period of time. Thus, the energy produced by the pyrotechnic element includes both high temperature and high pressure. One example of a pyrotechnic element suitable for the present invention includes a stoichiometric mixture of zirconium powder and potassium perchlorate combined with a nitrocellulose binder of 1–5 parts per 100 parts of the stoichiometric mixture as a suspension in an organic solvent. Another example would be a gelled form of nitroglycerin, which has the additional advantage of already being an approved drug for transdermal delivery applications.

As used herein, a "pyrotechnic ink" means any pyrotechnic element that is applied in a liquid form and which subsequently cures into the solid or gelled shape of the pyrotechnic element.

As used herein, the term "biological membrane" means the structure separating one area of an organism from another, such as a capillary wall, lining of the gut or the outer layer of an organism which separates the organism from it's external environment, such as epithelial tissue, skin, buccal mucosa or other mucous membrane. The stratum corneum of the skin may also be included as a biological membrane.

As used herein, "animal" or "organism" refers to humans and other living organisms including plants, to which the present invention may be applied.

As used herein, "analyte" means any chemical or biological material or compound suitable for passage through a biological membrane by the technology taught in this present invention, or by technology previously known in the art, of which an individual might want to know the concentration or activity inside the body. Glucose is a specific example of an analyte because it is a sugar suitable for passage through the skin, and individuals, for example those having diabetes, might want to know their blood glucose levels. Other examples of analytes include, but are not limited to, such compounds as sodium, potassium, bilirubin, urea, ammonia, calcium, lead, iron, lithium, salicylates, and the like.

As used herein, "transdermal flux rate" is the rate of passage of any analyte out through the skin of an individual, human or animal, or the rate of passage of any permeant, drug, pharmacologically active agent, dye, or pigment in and through the skin of an organism.

As used herein, "artificial opening" means any physical breach of the biological membrane of a suitable size for delivering or extraction fluid therethrough, including micropores.

The present invention is directed to a novel method and apparatus for creating microscopic holes, i.e. artificial openings 2, in a biological membrane 4, such as the stratum corneum of human skin, to increase the permeability of the biological membrane 4 with a minimal amount of sensation to the organism. Referring first to FIG. 1, the device of the present invention is shown generally at 10. The device 10 comprises essentially three elements: a substrate 20, a pyrotechnic element 30, and a trigger device 40. Generally, the function of the device 10 is to attach sufficiently to the surface of the biological membrane 4 and to make one or more artificial openings, or artificial openings 2, therein. More particularly, upon the detonation and resulting microexplosion of the pyrotechnic element 30 upon receipt of a detonation signal 42 from the trigger device 40, high temperature gases in combination with high localized pressures are directed at the targeted tissues when the micro-explosion is created in proximity to the biological membrane 4. This results in the thermal and kinetic energy removal of the targeted tissue and the resultant formation of an artificial opening 2.

As one skilled in the art will appreciate, the formation of the artificial opening 2 by the micro-explosion produced by the present invention will cause the artificial openings 2 to be formed in a very short time, which allows the microporation process to be carried out with little or no sensation to the subject organism. Based on the combustion front propagation of some of the common pyrotechnic compounds, a micro-charge such as those being discussed in the context of this invention could be expected to completely detonate within a few microseconds. The present invention concentrates the thermal and pressure energy produced by the explosion to the targeted areas of the biological membrane. For example, if the complete detonation/poration cycle is completed within less than 0.010 seconds, it can be shown via finite element thermal analysis that the thermal energy introduced into the biological membrane falls off with such a steep gradient that the peak temperature within 100 microns of the poration area never exceeds ~40' C, which is well below the human pain threshold for temperature if the targeted tissue is skin. More particularly, the present invention can create a pressure front which dissipates exponentially in the surrounding tissues after creating the desired pore, passing very little surplus energy into these adjacent tissues. In addition, the increased localized pressure produced by the micro-explosion of the pyrotechnic element 30 increases the combustion efficiency of the chemical reaction, which reduces the total amount of energy required to porate to a specific depth.

The substrate 20 of the device 10 has an upper surface 22 and a lower surface 24. The pyrotechnic element 30 may be positioned on either the upper of the lower surface 22, 24 of the substrate 20 but is shown disposed on the upper surface 22 of the substrate 20. The trigger device 40 is operatively connected to the pyrotechnic element 30 and is preferably on the same surface of the substrate 20 that the pyrotechnic element is disposed. The lower surface of the substrate 20 is in physical contact with a selected surface area of the biological membrane 4 so that the pyrotechnic element 30 is fixed in relation to the biological membrane 4. Fixing the pyrotechnic element 30 in relation to the surface of the biological membrane 4 allows for the controlled formation of artificial openings 2 having a shape within a predetermined range of both diameter and depth. To facilitate attachment of the device, a portion of the lower surface 24 of substrate 20 may have adhesive 25 attached thereto to facilitate attachment of the substrate 20 to the selected surface area of the biological membrane 4 and the energy transfer at this interface.

The substrate 20 of the device 10 is preferably formed from a non-conductive material. The substrate 20 may also preferably be chosen from material that chemically reacts and/or outgases in response to the thermal energy produced in the microexplosion of the pyrotechnic element 30 to produce enhancer substances, such as ammonia, or other beneficial byproducts. Any suitably substrate-forming material may be used. Suitably materials include, for example, but are not limited to, natural and synthetic polymers and gels, paraffin, waxes, hydrogels, sol-gels, glass, fabric, ceramic or paper layers. Additionally, appropriate substrates 20 may include but are not limited to low-melting point polymers and polymers impregnated, coated or microencapsulated with enhancers. The substrate 20 may be designed to contain pigments to effect an instantaneous tattoo application upon detonation of the pyrotechnic charges suitable for veterinary or cosmetic tattoos.

The substrate 20 preferably has a thickness of approximately 10 microns to 1000 microns. More particularly, it is preferred that the substrate 20 has a thickness of approximately 10 to 500 microns. In the embodiment where the pyrotechnic element is disposed within a hole fabricated in the substrate 20 layer, the thickness of the substrate 20 may be used during the manufacturing process to control the amount of explosive material placed at each site, the shape of the resulting pressure front created when the charge is detonated, and the resulting geometries of the formed pore. The The trigger device 40 may be any means known to one skilled in the art for activating a pyrotechnic element 30. These means include, but are not limited to, electrical triggers, percussive triggers, thermal triggers, optical triggers and the like. The only requirement for a suitable trigger device 40 for the present invention is the requirement that the trigger device 40 conduct a trigger signal 42 to the pyrotechnic element 30 capable of triggering the detonation of the pyrotechnic element 30. The preferred trigger device 40 is an electrically conductive element 44 disposed in contact with the pyrotechnic element 30 which can conduct an electrical detonation signal 46 to the pyrotechnic element 30. The source of the electrical detonation signal 46 may be any local or remote pulse source.

An example of an optical trigger is a laser beam emitted from a laser source, such as a laser diode. For example, pyrotechnic ink is screen printed in dots on a clear plastic film substrate. In use, the substrate is placed against the surface of the biological membrane with the ink dots facing the membrane. Detonation of the pyrotechnic ink is triggered by illuminating the dots with a laser beam through the clear plastic film substrate. Sufficient heat is achieved with a laser pulse of sufficient laser beam power and wavelength. Alternatively, the pyrotechnic ink is integrated with a photothermal material or dye that absorbs the laser beam energy to heat up and trigger detonation even faster. A laser beam trigger has an advantage of requiring no electrical connections to the pyrotechnic elements.

The same conductive elements 44 can also be used after the artificial opening formation process as electrodes for additional permeation enhancement techniques such as iontophoresis and/or electroporation, or even as the connections to a piezo-element placed within the device to provide a sonic energy source. A more detailed description of how all of these different enhancement techniques can be coupled with a pore formed in the skin is provided in the pending international patent application PCT WO98/29134, "Microporation of Tissue for the Delivery of Bioactive Agents." Similarly, the conductive elements that connect to the pyrotechnic elements are also useful, after the artificial openings are formed, as electrodes as part of a sensor, such as an electrochemical bio-sensor, for detecting an analyte in the biological fluid being collected from the artificial openings. Suitable materials for the conductive elements for use both as triggering elements and electrodes for electrochemical detection are platinum, platinum/carbon and carbon.

While the electrically conductive element 44 may be disposed on either the upper or the lower surface 22, 24 of the substrate, the electrically conductive element 44 of the present invention is preferably disposed on the upper surface 22 of the substrate 20. This advantageously results in the electrically conductive element 44 being separated from the surface of the biological membrane 4 by the interposing substrate 20. This prevents the electrically conductive element 44 from contacting the surface of the biological membrane and resultantly being adversely affected by the undesirable effects of bodily fluids, such as sweat, body oil, and the like, which are present on the surface of most biological membranes 4.

Figure 2:
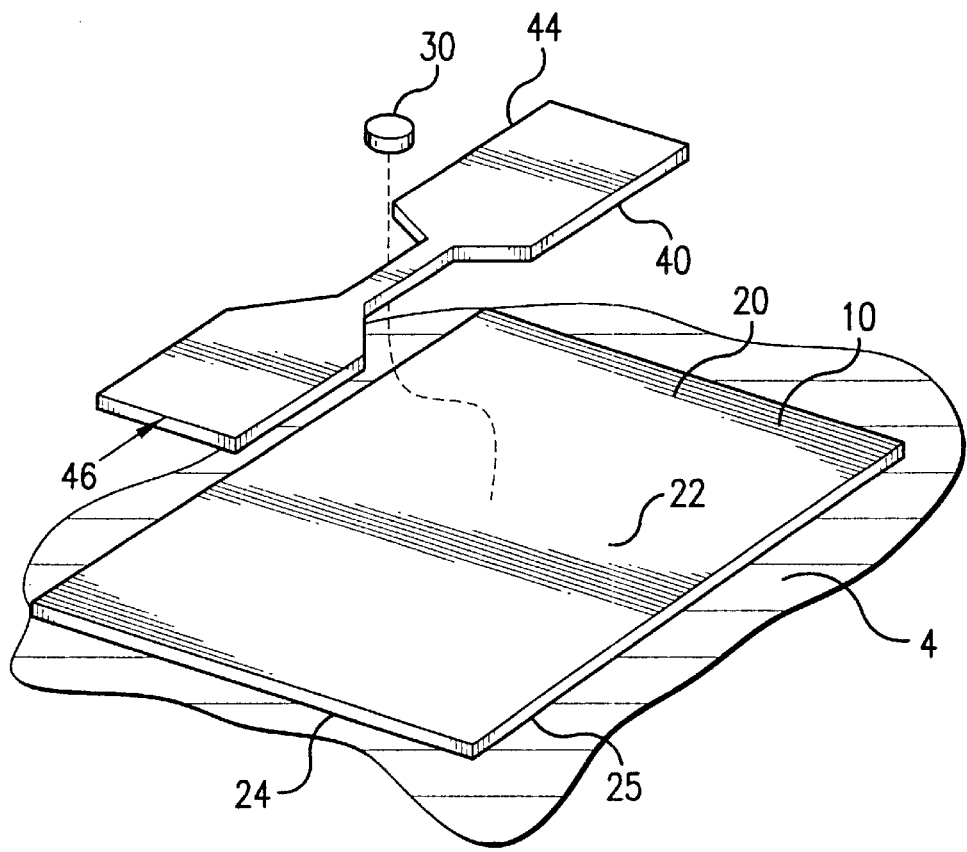
FIG. 2 is an exploded perspective view of the device shown in FIG. 1.
Figure 3:
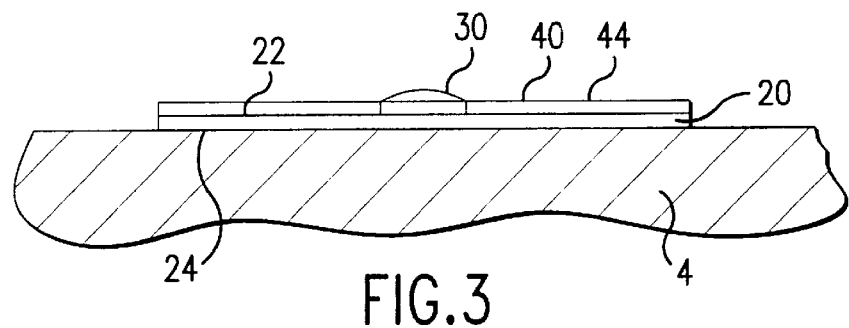
FIG. 3 is a cross-sectional view of the device shown in FIG. 2.

Referring now to FIGS. 2 and 3, a conductive element 44, such as a carbon trace, is applied to the upper surface 22 of the substrate 20 using techniques known to one skilled in the art. A pyrotechnic element 30 is then deposed on the conductive element 44 to complete the necessary connection of the pyrotechnic element 30 and the conductive element 44. This step may be performed by disposing, such as by screening, a measure of pyrotechnic ink on the conductive element 44. When the pyrotechnic ink cures, the pyrotechnic element 30 is in operative contact with the trigger device 40. Because the substrate 20 is interposed between the surface of the biological membrane 4 and the pyrotechnic element 30 in this embodiment, it is preferred that the substrate 20 used for this embodiment be of a type that is readily volatized under the forces of the micro-explosion of the pyrotechnic element 30 so that sufficient energy is directed to the biological membrane 4 to form the desired artificial opening 2. A artificial opening 2 formed using a device 10 of this embodiment would have the general shape shown in FIG. 4 after the micro-explosion had occurred (assuming that the pyrotechnic element had a generally round cross-sectional shape). Enhancers may be preferably incorporated into the substrate 20 to enhance the resulting transdermal flux rate.

Figure 5:
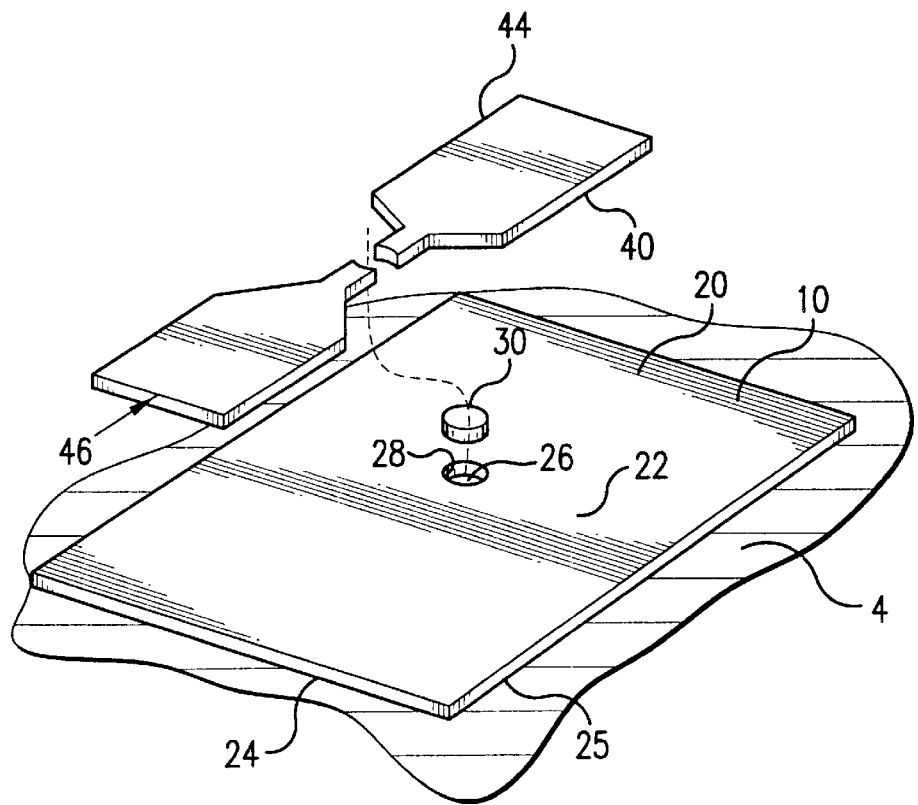
FIG. 5 is an exploded perspective view of device according to another embodiment of the invention.
Figure 6:
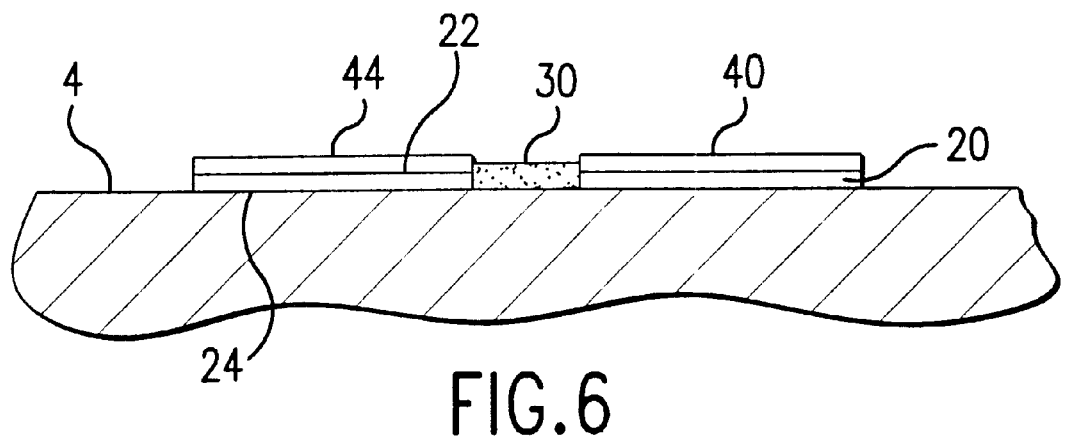
FIG. 6 is a cross-sectional view of the device shown in FIG. 5.
Figure 7:
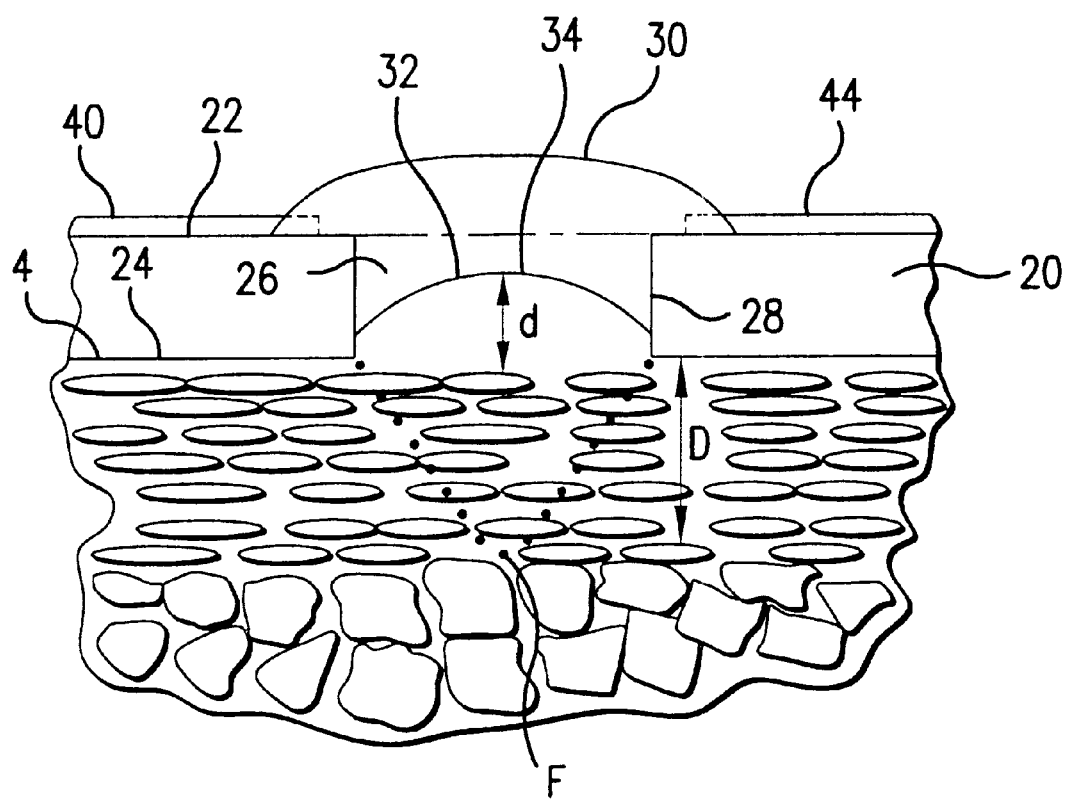
FIG. 7 is a partial cross-section view of a device according to another embodiment of the invention.

Referring now to FIGS. 5–7, devices according to second embodiment and third embodiments of the present invention are shown. In both embodiments, the substrate 20 has at least one aperture 26 extending through the substrate 20. This aperture 26 has an aperture wall 28 of a predetermined shape so that a desired-shaped artificial opening 2 may be formed. As one skilled in the art will appreciate, by changing the shaped of the aperture wall, the form of the micropore may be altered. For example, a star shaped aperture wall of the aperture may be used to form a star shaped micropore. In a further example, a slot shaped aperture wall may be used to form a slot shaped micropore. Pores of a particular shape may have cosmetically preferable properties while still facilitating the desired transdermal flux rates. Preferably however, the aperture wall of the aperture has a square or round cross-sectional shape. These shapes allow for the ready determination, using calculations know to one skilled in the art, of the resulting depth and diameter of the formed micropore based upon the distance the pyrotechnic element is spaced from the biological surface and the known explosive power of the pyrotechnic element.

The conductive element 44, which is exemplified by a carbon trace, is preferably applied to the upper surface 22 of the substrate 20 so that it is in contact with an aperture 26 of the substrate 20. A pyrotechnic element 30, preferably initially in the form of a pyrotechnic ink, is then deposed on each aperture 26 therein in contact with the conductive element 44 to complete the necessary connection of the pyrotechnic element 30 and the conductive element 44 of the trigger device 40.

The primary difference between the second embodiment and third embodiment of the present invention is the disposition of the pyrotechnic element 30 within the aperture 26 in relation to the surface of the biological membrane 4. In the second embodiment shown in FIG. 6, the pyrotechnic element 30 may substantially fill the aperture 26 of the substrate 20 so that the pyrotechnic element 30 is in close physical contact with the surface of the biological membrane 4. In the third embodiment, as best shown in FIG. 7, the pyrotechnic element 30 extends only partially down inside the aperture 26 of the substrate 20 from the upper surface 22 so that the bottom surface 32 of the pyrotechnic element 30 is spaced a distance (d) from the lower surface 24 of the substrate 20 so that the aperture 26 is only partially filled.

If the pyrotechnic element 30 of the device 10 is in close physical contact with the selected surface area of the biological membrane 4, as is shown in FIGS. 5 and 6, the explosive force is directed to the general surface of the biological membrane 4 on which the pyrotechnic element 30 is in contact. The resultant micropore 4 formed from the micro-explosion of the pyrotechnic element 30 is similar to that shown in FIG. 4. This embodiment is efficient in that no portion of the force is wasted in volatilizing the substrate 20. The temperature, pressure, and velocity of materials produced by the pyrotechnic element 30 and the resultant depth and diameter of the formed artificial opening 2 is dependent in this embodiment upon the nature (i.e., the physical properties and efficiency of the explosive pyrotechnic element 30 used per unit weight) of the pyrotechnic element and the quantity of pyrotechnic element 30 used.

Figure 8:
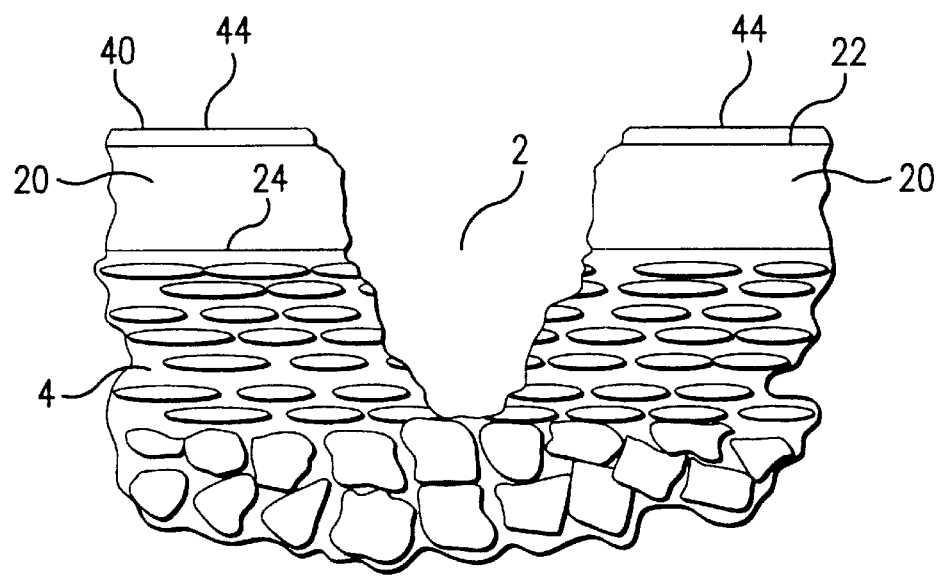
FIG. 8 is a partial cross-sectional view of the device shown in FIG. 7 showing the formation of an opening in the biological membrane.

Preferably however, and as shown in FIG. 7, the bottom surface of the pyrotechnic element 30 is spaced from the lower surface 24 of the substrate 20. In this embodiment, it is preferred that pyrotechnic ink be used for the formation of the pyrotechnic element 30 so that a ready-formed shaped charged surface 34 is formed on the bottom surface 32 of the pyrotechnic element 30 when the pyrotechnic ink cures into the pyrotechnic element 30. Due to surface tension acting on pyrotechnic ink when the ink cures from the fluid state, the bottom surface 32 of the pyrotechnic element 30 will arch toward the upper surface 22 of the substrate 20 and will have a generally parabolic shape in cross-section. This shaped charged surface 34 may be made by mechanical means after the pyrotechnic element 30 is disposed on and into the aperture 26, but the use of surface tension acting on the pyrotechnic ink as it cures is the preferred means for forming a generally parabolic shaped charged surface 34 of the third embodiment of the present invention. When the pyrotechnic element 30 is detonated, the general parabolic shaped charge surface 34 causes the generation of high temperature, high pressure, and high velocity materials at the focus (F) of the shaped charge explosion. Spacing the pyrotechnic element 30 from the lower surface 24 of the substrate 20, which in operation is coincident with the surface of the biological membrane 4, allows the focus of the micro-explosion to be directed to the depth D desired within the biological membrane 4. As shown in FIG. 8, this results in an artificial opening 2 extending therethrough the biological membrane 4. Additionally, because the location of the focus of the shape charged surface 34 may be readily calculated from standard equations that consider the shape of the parabolic surface, the artificial opening 2 may be advantageously formed without damaging the underlying tissues, such as the epidermis of the skin when the stratum corneum of the skin is microporated.

Figure 4:
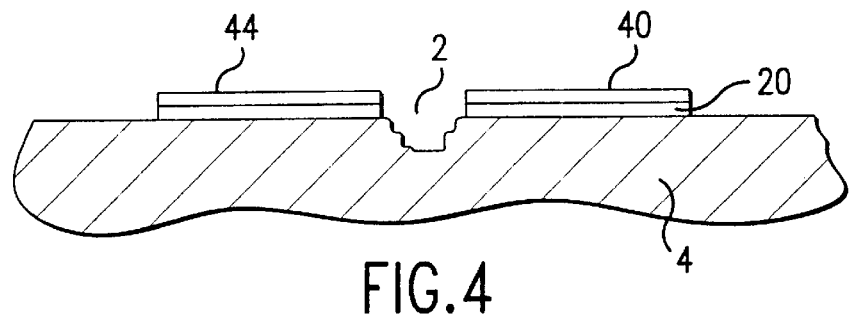
FIG. 4 is a cross-sectional view similar to FIG. 3 and showing the device and underlying biological membrane after the pyrotechnic element is detonated.

As noted above the pyrotechnic element 30 is shaped to form a micropore of specified shape, diameter, and depth. The shape of the formed micropore of the present invention is preferably cone shaped as shown in FIGS. 4 and 8. The formed micropores preferably have a diameter in the range of 1–1000 $\mu$m and a depth in the range of 1–3000 $\mu$m. More particularly, the micropores preferably have a diameter in the range of 10–600 $\mu$m and a depth in the range of 10–1000 $\mu$m.

Figure 9:
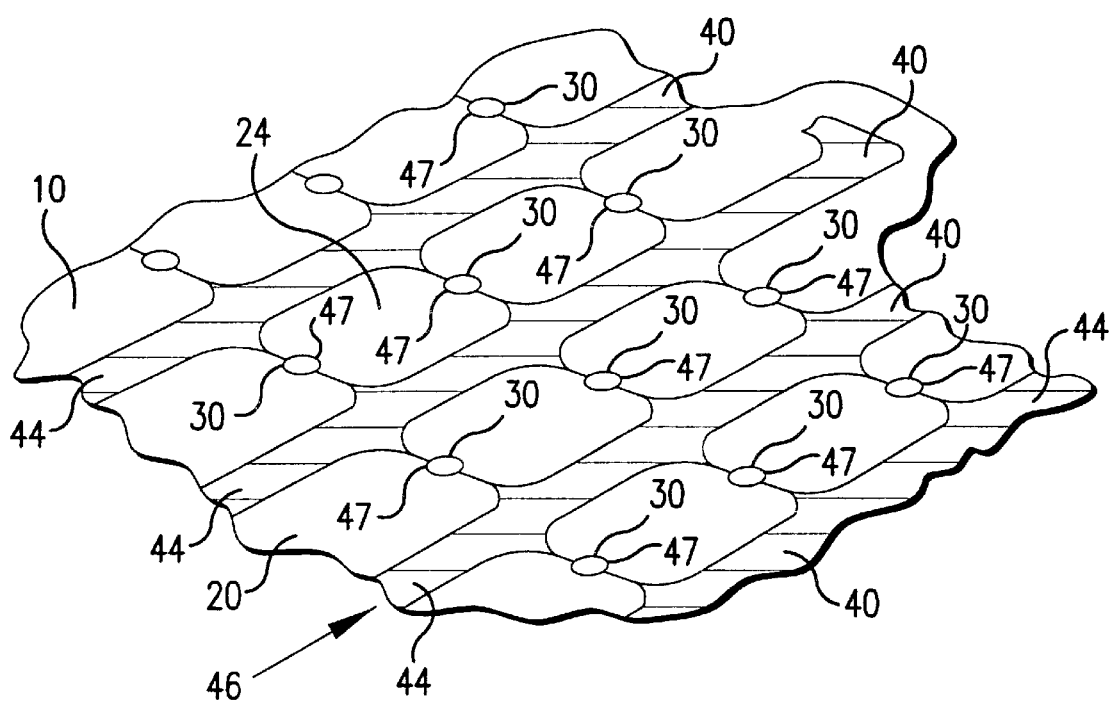
FIG. 9 is a partial cross-section view of a conductive network disposed on the upper surface of the substrate in contact with a plurality of pyrotechnic elements for triggering the detonation of a plurality of pyrotechnic elements to form a plurality of openings in the biological membrane.
Figure 10:
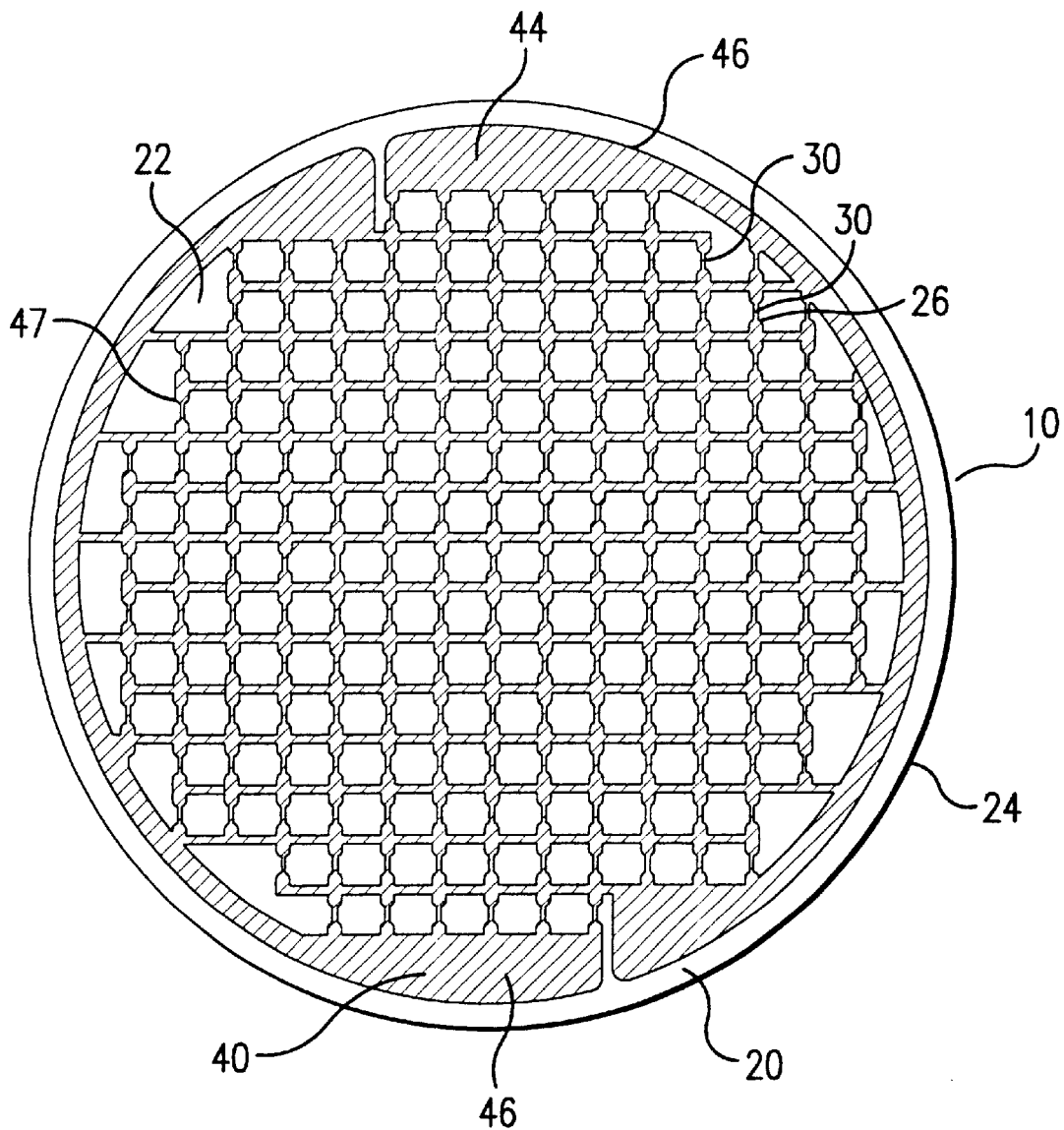
FIG. 10 is a top view of a device having a conductive network disposed on the upper surface of the substrate in contact with a plurality of pyrotechnic elements for triggering the pyrotechnic elements to from a plurality of artificial openings.

FIGS. 9 and 10 illustrate that the electrically conductive elements 44 are arranged in a network 46. Specifically, the conductive elements 44 are connected to the respective apertures 26 are linked together in a conductive network 46 so that the plurality of pyrotechnic elements 30 disposed into the plurality of apertures 26 within the substrate 20 of the device 10 may be simultaneously or sequentially detonated upon receipt of the electrical detonation signal(s) 46 applied across the electrodes to the network 46. For a sequential detonation, it may be desirable to isolate some circuits within the conductive network 46 and trigger the detonation sequence in a predetermined fashion programmed into the trigger device 40. Alternatively, as described above, using slightly different length small traces of fuse material to connect each detonator to one or more pyrotechnic elements could be used to create a preset sequential detonation.

Figure 11:
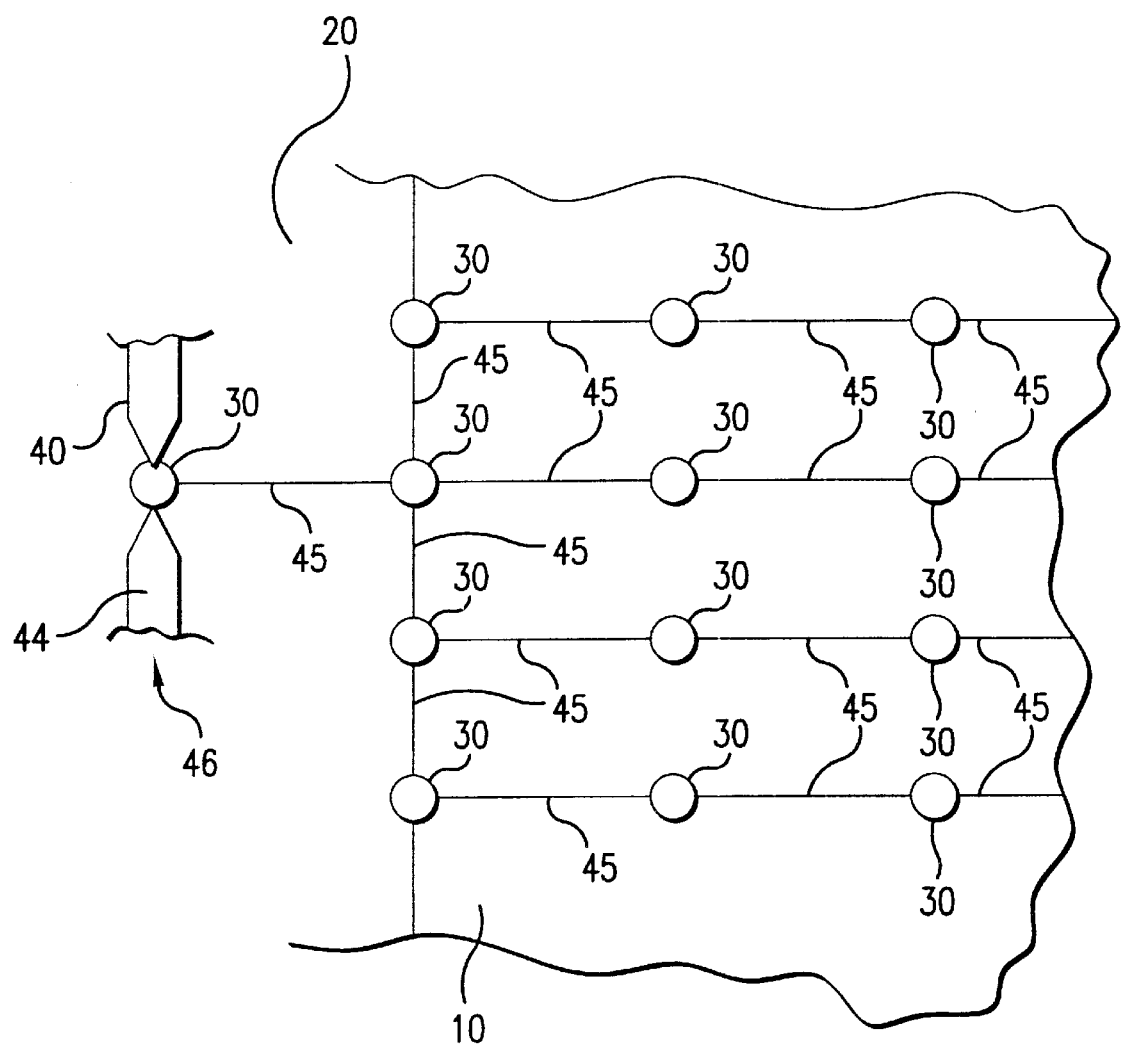
FIG. 11 is a partial, top view of a device illustrating a detonating scheme employing traces of pyrotechnic compound disposed on the substrate between adjacent pyrotechnic elements.

For an array of pyrotechnic elements disposed on a device, as shown in FIG. 11, it is also possible to use a conductive element 44 exemplified by the conductive carbon trace described herein to first detonate a single pyrotechnic element 30 and then by having placed within the array of pyrotechnic elements 30 a series of small traces 45 of a selected pyrotechnic substance which interconnects them, allow this first pyrotechnic element 30 detonation to initiate the subsequent detonation of all of the other elements 30. This design simplifies the manufacture of the electrically activated trigger device 40 and can potentially result in a lower cost product.

Figure 12:
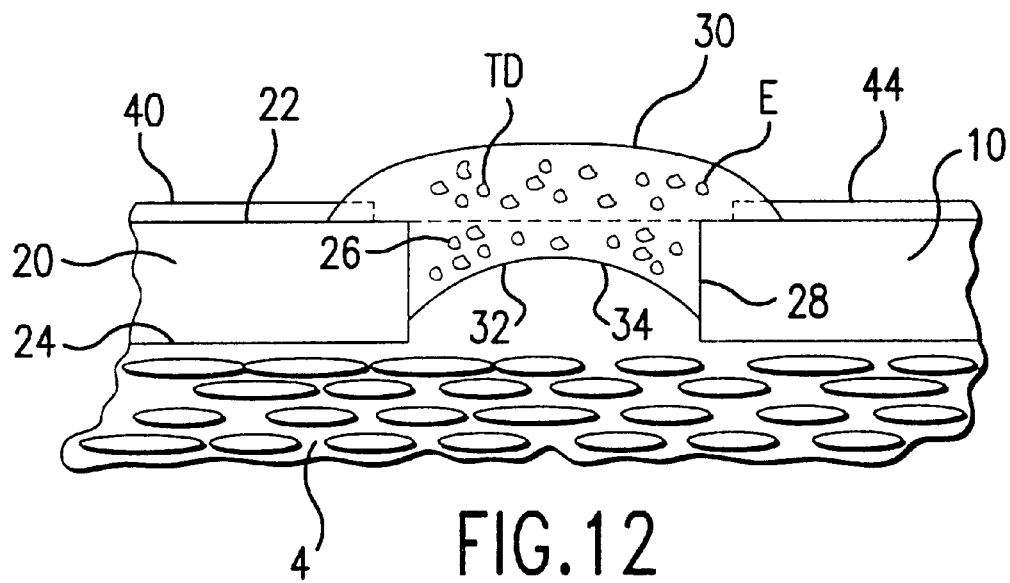
FIG. 12 is a partial, cross-section view of a device showing the pyrotechnic element combined with one or more permeants or enhancers to be introduced into the organism during the explosive formation of the artificial opening.

The device 10 of the present invention may also be combined with permeants, chemical enhancers (E), therapeutic drugs (TD), or any combination of chemicals. Referring to FIG. 12, chemical enhancers E, therapeutic drugs TD, and/or other desired chemicals may be advantageously combined with the pyrotechnic element 30. This allows the added chemical or compound to be forcefully introduced into the artificial opening 2 by the energy supplied by the detonation of the pyrotechnic element 30. For example, the substrate 20 may be fabricated from powder of biodegradable polymer micro-particles which contain a permeant, e.g., a therapeutic compound such as a vaccine antigen, DNA, or protein. Upon detonation of the pyrotechnic element 30, the bonds between the individual micro-particles forming the substrate 20 are broken and are subsequently driven at high velocity into the walls of the artificial opening 2 being formed. Some of these particles will penetrate through cell walls and come to rest within the interior of an intact and still viable cell. This momentary disruption of the cell wall by the shock wave and the kinetic impact of the particle have been shown to be an effective method for delivering macromolecules and micro-particles.

Figure 13:
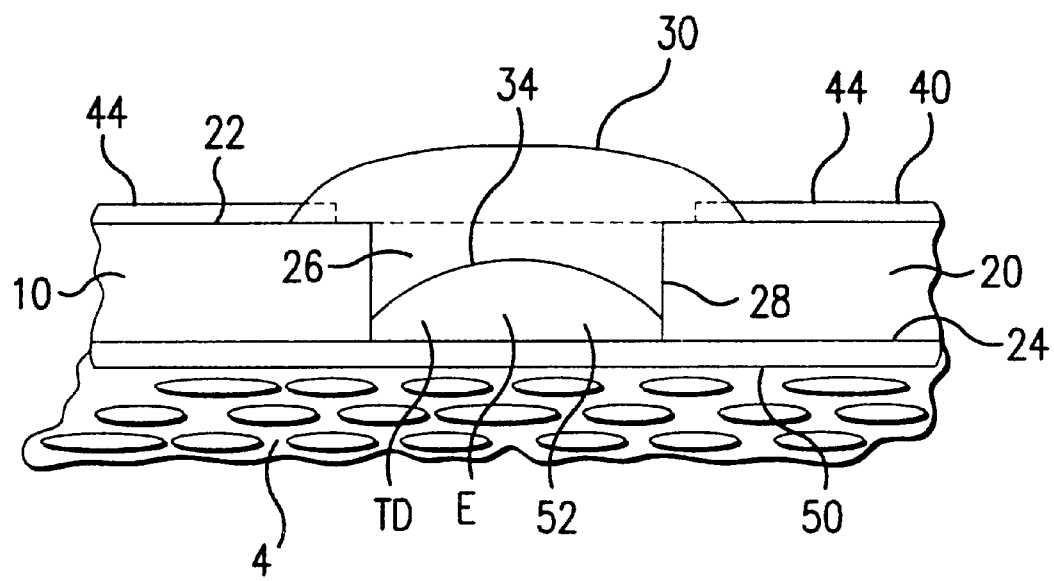
FIG. 13 is a partial, cross-section view of a device featuring a reservoir for permeants or enhancers disposed between the pyrotechnic element and the biological membrane.

Referring now to FIG. 13, an alternative embodiment of the device 10 of the present invention is shown. The device shown in FIG. 13 comprises a thin walled membrane 50 attached to the lower surface 24 of the substrate 20. As one skilled in the art will appreciate, a reservoir 52 is defined by the shaped charged surface 34 of portion of the pyrotechnic element 30 extending within the aperture 26, the aperture walls 28 of the aperture 26, and the thin walled membrane 50. The reservoir 52 may contain chemical enhancers (E), therapeutic drugs (TD), or other beneficial substances. This reservoir 52 is explosively breached by the energy supplied by the detonation of the pyrotechnic element 30 which resultantly causes the stored substance to be forcefully delivered into the organism past the biological membrane 4 via the formed artificial opening 2.

Figure 14:
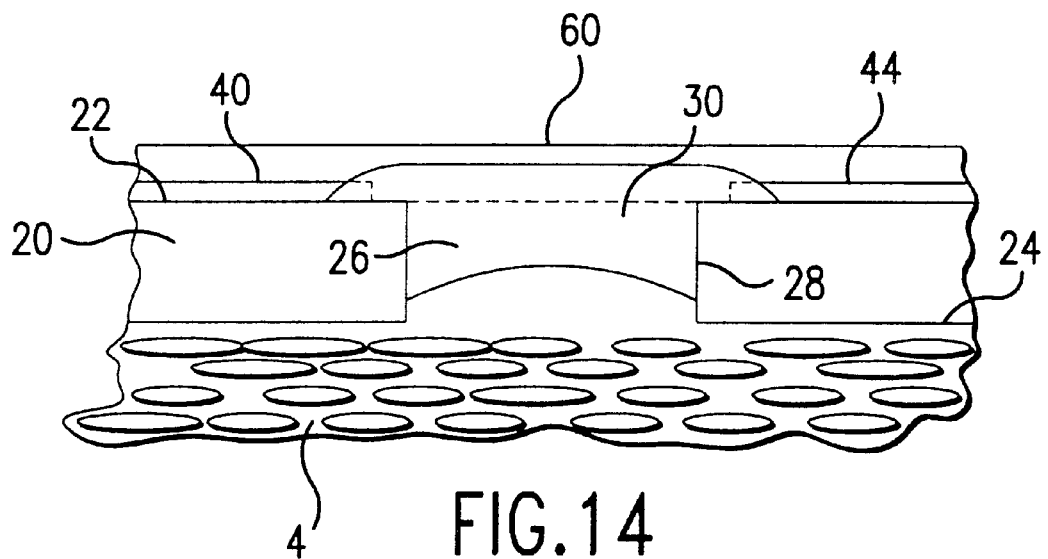
FIG. 14 is a partial, cross-section view of a device showing a cover film disposed on the pyrotechnic element.

Referring now to FIG. 14, a cover film 60 overlays the top surface of the device of the present invention, covering at least the pyrotechnic element 30 and optionally the trigger device 40. This cover film 60 helps to contain and focus the force of the microexplosion of the pyrotechnic element 30 such that the heat and pressure generated by the micro-explosion is directed at the targeted tissue and is not vented to the surrounding atmosphere. Additionally, by containing the micro-explosion, the cover film 60 acts as a safety feature as any material that would be potentially ejected by the force of the micro-explosion would be contained. The cover film 60 is preferably formed from thermally non-conductive, high-melting point material, such as a suitable polymer, ceramic, metal and the like.

The aperture 26 in the configuration of FIG. 14 is optional. For example, the substrate 20 is a matrix patch-like member that has indent areas on its upper surface, but otherwise is a contiguous element (without the aperture 26 as shown in FIG. 14).

The substance for the pyrotechnic elements is screen printed on the substrate 20 into the indented areas. The detonation electrode material for the trigger device is applied to the surface above the pyrotechnic elements as shown in FIG. 14. The cover film is then applied to the top surface of the device over the detonation electrode material of the trigger device. Consequently, the substrate 20 includes a region between the pyrotechnic elements 30 and the surface of the biological membrane that acts as a spacer. When the pyrotechnic elements are detonated, a shock wave is created through the substrate 20 forming the artificial opening(s). In addition, the substrate 20 is optionally treated with one or more enhancers or permeants, etc., so that upon detonation, the treated substrate matrix material is driven into the biological membrane with the micro-explosion.

In use, the device 10 of the present invention forms artificial openings 2 into a selected area of a biological membrane 4 for enhancing the permeability of the biological membrane 4. The operator simply connects the lower surface 24 of the substrate 20 of the device 24 on the surface of a biological membrane 4 and then triggers the trigger device 40 of the device 10. Triggering of the pyrotechnic element 30 (of sufficient energy to penetrate the biological membrane to a desired depth) causes an artificial opening 2 to form that extends into or through the biological membrane 4.

A permeant, such as a therapeutic drug, may be applied to the formed artificial opening 2 for delivery of the therapeutic drug or compound from without the biological membrane 4 into the organism. In still another use for the formed artificial opening 2, fluids or analytes may be withdrawn from the organism via the artificial opening 2. In the absence of the barrier function normally attributable to the biological membrane 4, such as the stratum corneum of the skin, the percutaneous transport of the therapeutic drug or the analytes is enhanced.

Figure 15:
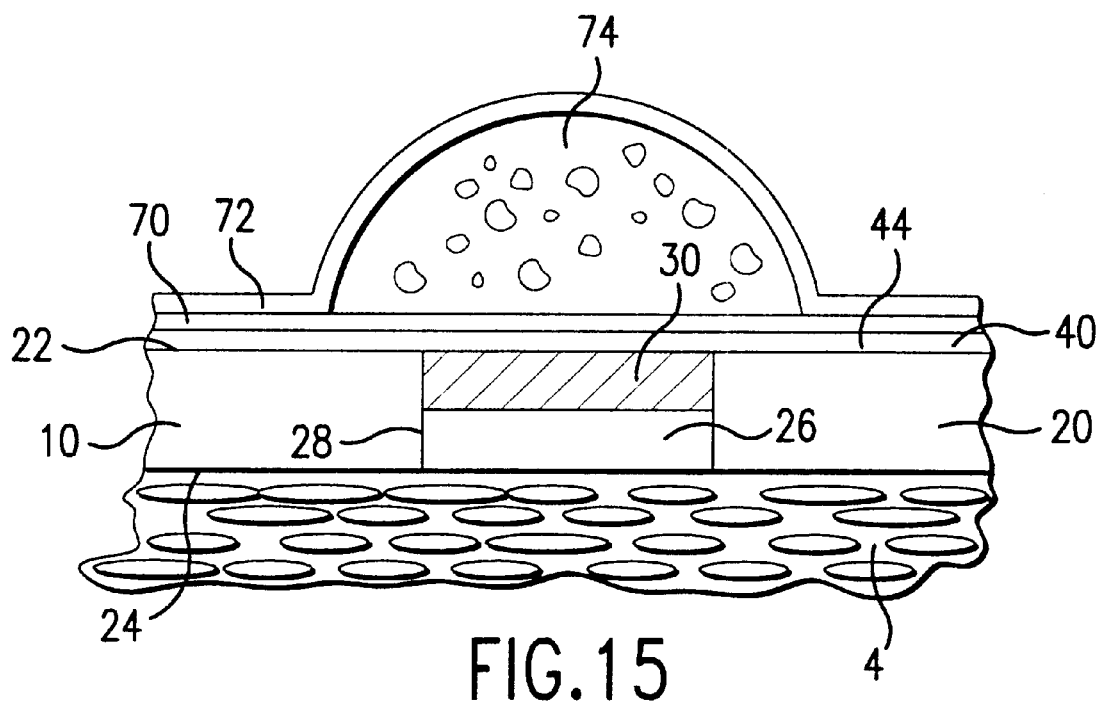
FIG. 15 is a partial, cross-section view of a device featuring a reservoir cavity for permeants or enhancers disposed between a first film layer and a second film layer.

As shown in FIG. 15, a separate reservoir may be integrated into the device 10 for delivering the permeant to the formed micropore. A first film layer 70 is disposed on the upper surface 22 of the substrate 20, and preferably over the pyrotechnic element 30 and the trigger element 44. A second film layer 72 is secured to peripheral portions of the first film layer 70 to define a reservoir cavity 74 that contains one or more permeants. The reservoir cavity 74, and more particularly the first film layer X, may be breached simultaneously with the pore forming detonation of the pyrotechnic element 30.

Figure 16:
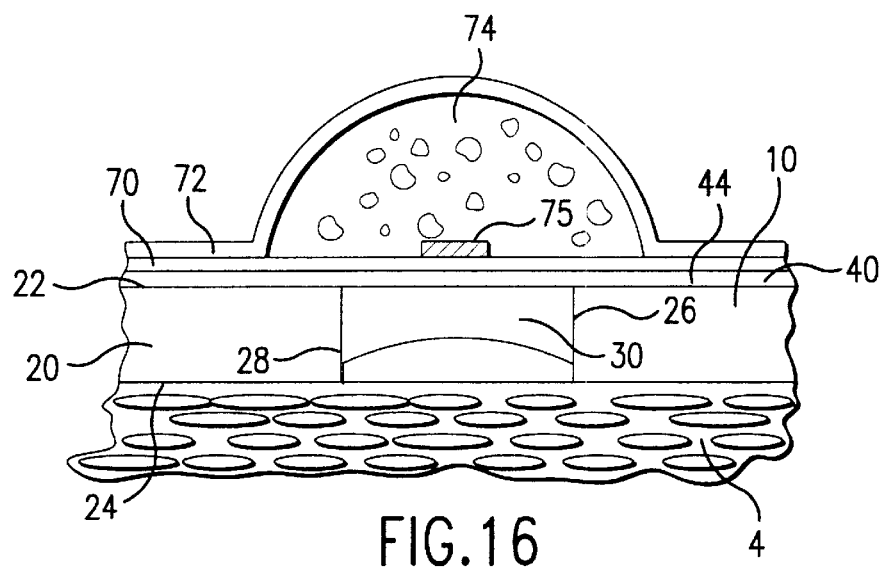
FIG. 16 is a partial, cross-section view of another device featuring a reservoir cavity for permeants or enhancers disposed between a first film layer and a second film layer.

Alternatively, as shown in FIG. 16, the first film layer 2 may be kept intact during the detonation of the pyrotechnic element 30, and then opened up at a later time by either the detonation of a separate pyrotechnic element 75 placed on the first film layer 70, or the activation of an optically or electrically heated element disposed on the first film layer 70 as disclosed in commonly assigned U.S. Pat. No. 5,885,211.

For some applications a plurality of separately addressable reservoirs 74 may be used to allow for the sequential administration of several different permeants which otherwise may not be compatible to be placed in the same formulation together. In this case it can be advantageous to isolate each permeant to a selected artificial opening 2 or set of artificial openings 2 thereby insuring that no mixing of the incompatible permeants occurs outside of the organism's body. One example of where this is useful is when an dilute ammonia (NH3) based permeation enhancer is being used to permealize the capillary walls for the delivery of a labile protein or peptide such as erythropoietin or parathyroid hormone In this case the value of using the NH3 compound has been shown dramatically in clinical studies, however the highly alkaline properties of the NH3 are known to be detrimental to the integrity of the therapeutic permeant. By isolating each of these substances in separate reservoir cavities 74, and then using separate pores to introduce then into the organism, the NH3 enhancer can be given a enough time to diffuse down to the capillary bed, perform its permealization function, and then be effectively neutralized by the huge buffering capacity of the organisms internal fluids. Then, with the pH in the tissue essentially back to normal, the therapeutic permeant can be introduced into a set of proximally adjacent pores 2 which allow diffusion to the very same capillaries permealized by the NH3. Various patterns can be used, for example a single pore 2 to deliver the NH3 can be surrounded by a circle of pores 2 delivering the therapeutic permeant. Similarly, alternating rows of pores 2 could be used, or any pattern designed to deliver the appropriately effective amounts of the respect permeants which can be expected to vary from one application to the next.

The manufacture of this separate reservoir technology can be achieved using common die-stamping, printing, lithographic, and heat-bonding techniques. For example, the substrate 20 could first have the pyrotechnic elements 30 and the trigger device 40 placed on the upper surface of the substrate 20 via screen-printed or inkjet printing technologies. As described above, an enhancer may be combined with the pyrotechnic element 30. Here, the NH3 enhancer, exemplified by a solid form of ammonium carbonate, is deposited directly on those pyrotechnic elements 30 designated to deliver the NH3 into the organism. The first film layer 70 is then placed over the entire assembly and thermally bonded with an indexed thermal die to form isolated pockets around the NH3 active portions. This first film layer 70 is designed to withstand the detonation of the pyrotechnic elements 30 without rupturing in the areas of the NH3 compound. When the pyrotechnic elements 30 that are combined with ammonium carbonate are detonated, the heat of the micro-explosion causes the ammonium carbonate to break down into NH3 and H2O and delivers the enhancer into the walls of the pore 2 formed very efficiently. The second film layer 72 is then deposed on the first film layer to form at least one reservoir cavity 74 containing the desired therapeutic permeant The initial pyrotechnic element 30 detonation may allow the rupture of this reservoir cavity 74, or alternatively, separate thermal or PE detonations can be used to form openings in this reservoir cavity 74 to allow the stored therapeutic permeant access to the pores 2 formed beneath it in the organism.

Similarly, separately assessable reservoir cavities 74, which can be sequentially opened, are useful to tailor the pharmacokinetics of a permeant to the desired values over time. For example, the device 10 could be set up to be responsive to the measurement of some analyte withdrawn from one or more artificial openings 2, such as glucose, and when indicated, to open up a reservoir cavity 74 containing insulin to deliver a preset unit dosage of insulin in a closed loop fashion. Another application could be the periodic administration of flux enhancers designed to facilitate the extraction of fluids or analytes over extended periods of time, where each new dose of the enhancer would be tailored to act for some predetermined duration, allowing a long term monitoring system to utilize the same artificial opening, while still getting the benefits of an enhancer technology which in itself may be relatively short acting.

Figure 17:
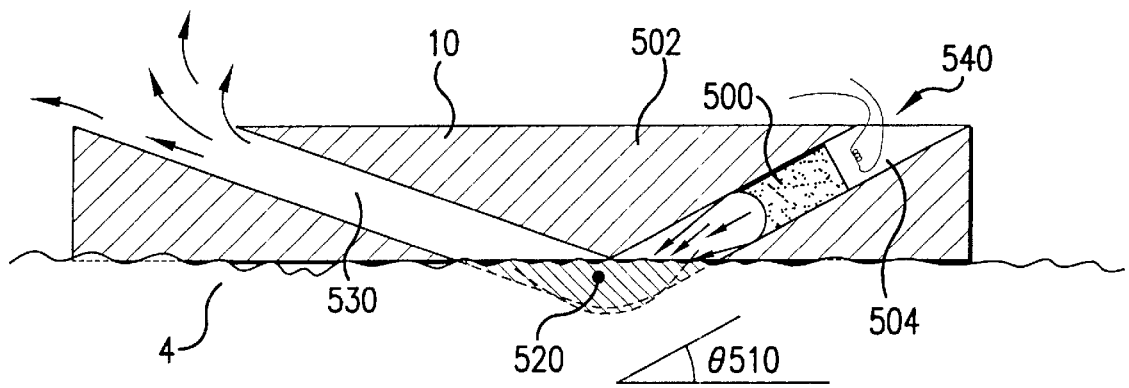
FIG. 17 is a partial cross-section view of a device featuring angled orientation of the pyrotechnic element.

FIG. 17 illustrates still another embodiment of the invention wherein the angular position of the pyrotechnic element is controlled to affect the shape of the artificial opening so formed. As explained above, positioning the pyrotechnic element at some specified distance from the surface of the biological membrane may be used advantageously as one way of controlling the amount of energy presented to the surface of the biological membrane. In the case where a shaped charge pyrotechnic element is utilized, this spacing may be selected to place the focal point of the peak pressure precisely where desired in reference to the surface of the biological membrane.

Similarly, angular positioning of the shaped charge pyrotechnic element to the surface of the biological membrane can be used to control the shape of the pore formed and the amount of energy coupled into the targeted and adjacent tissues. FIG. 17 shows a narrowly focused shaped charge pyrotechnic element 500 positioned in a cavity or channel 504 of a substrate member 502 at an angular position with respect to a lower surface of the substrate member 502, and consequently of the surface of the biological membrane. The trigger or detonator element 540 detonates the pyrotechnic element 500, so that the direction of the focused pressure wave is brought to the surface of the biological membrane at a shallow angle 510. This configuration will produce a trench-like opening 520, literally blowing the targeted tissue away while coupling very little energy into the adjacent tissues. An escape port or channel 530 is also optionally provided to assist in the removal of the waste gases and tissue fragments. The shape of the channel 504 in which the pyrotechnic element 500 resides and the shape of the escape channel 530 also contribute to forming a desired pressure focal points and assist in the extraction process of the material. These same channels can also be used to either extract a fluid from or deliver a permeant into the organism.

It should be understood the device comprising one or more pyrotechnic elements may also include structures to collect biological fluid and manage its movement to a sensor that is responsive to one or more analytes.

Although the present invention has been described with reference to specific details of certain embodiments thereof, it is not intended that such details should be regarded as limitations upon the scope of the invention except as and to the extent they are included in the accompanying claims.

We claim:

1. A device for forming at least one opening in a select area of a biological membrane for transmembrane transport, comprising:
   a) a substrate having an upper surface and a lower surface;
   b) a pyrotechnic element disposed on either the upper or lower surface of said substrate, the pyrotechnic element having an explosive potential sufficient to form said opening; and
   c) a trigger device coupled to said pyrotechnic element.

2. The device of claim 1, wherein the pyrotechnic element is spaced from the lower surface of the substrate by a predetermined distance.

3. The device of claim 1, wherein the pyrotechnic element is shaped to form at least one opening of a specified shape.

4. The service of claim 1, wherein the pyrotechnic element comprises an explosive potential to form at least one opening of a specified depth into or through the biological membrane.

5. The device of claim 1, wherein said pyrotechnic element is disposed on the upper surface of said substrate.

6. The device of claim 1, wherein the trigger device comprises a laser source that emits a laser beam onto the pyrotechnic element.

7. The device of claim 1, wherein said substrate has at least one aperture extending through said substrate, each aperture having a perimeter wall, and wherein the pyrotechnic element is disposed on said substrate proximate the aperture.

8. The device of claim 7, wherein the perimeter wall of the aperture of said substrate has a predetermined shape.

9. The device of claim 7, wherein a portion of said pyrotechnic element extends into said aperture to form a shaped charge surface that is spaced apart a predetermined distance from the lower surface of said substrate so that the shape, diameter and depth of the artificial opening is controlled.

10. The device of claim 9, wherein the shaped charge surface of said pyrotechnic element has a curved shape in cross-section, said curved shape extending upwardly toward the upper surface of said substrate.

11. The device of claim 1, wherein said pyrotechnic element is combined with a permeant and/or an enhancer.

12. The device of claim 1, wherein said substrate is treated with a permeant and/or an enhancer.

13. The device of claim 12, wherein said permeant is a pigment designed to be placed in the skin of an organism for the purpose of creating a tattoo.

14. The device of claim 1, and further comprising a reservoir for containing one or more permeants arranged above the pyrotechnic element.

15. The device of claim 14, and further comprising an aperture the substrate beneath the pyrotechnic element.

16. The device of claim 1, wherein the trigger device comprises at least two electrically conductive elements that are electrically coupled to the pyrotechnic element.

17. The device of claim 1, the at least two conductive elements are part of a sensor for detecting an analyte in biological fluid collected from the artificial openings.

18. The device of 16, wherein the at least two conductive elements are suitable for connection to electrical energy for treating the biological membrane with iontophoresis or electroporation energy.

19. The device of claim 1, and further comprising a plurality of pyrotechnic elements, wherein said trigger device comprises a network of electrically conductive elements, the conductive network making electrical contact with the plurality of pyrotechnic elements to conduct electrical energy to each pyrotechnic element.

20. The device of claim 1 and farther comprising a plurality of pyrotechnic elements, wherein traces of pyrotechnic compound are disposed on the substrate in proximity to each of the pyrotechnic elements, wherein said trigger device comprises a conductive network disposed on said substrate, the conductive network making electrical contact to at least one of pyrotechnic elements to conduct electrical energy to said at least one pyrotechnic element which when detonated, triggers the detonation of the small traces of pyrotechnic compound such that the connected pyrotechnic elements are in turn also detonated.

21. The device of claim 1, further comprising a film disposed over the pyrotechnic element.

22. The device of claim 1, further comprising a first film layer and a second film layer, wherein said first film layer is connected to portions of the upper surface of said substrate so that said trigger device and said pyrotechnic element are sealed between said first film layer and the upper surface of the substrate, wherein said second film layer is connected to a portion of the first film layer to form at least one reservoir cavity so that permeant stored is the reservoir cavity may be delivered to select ones of artificial openings formed in the biological membrane.

23. The device of claim 1, wherein the pyrotechnic element is positioned within or on the substrate at an angle with respect to a lower surface of the substrate.

24. The device of claim 23, wherein the substrate comprises a channel arranged at an angle with respect to a lower surface of the substrate, wherein the pyrotechnic element is positioned within the channel.

25. The device of claim 23, and further comprising a channel through the substrate to provide a path to release pressure and material caused by the microexplosion.

26. The device of claim 1, and further comprising a channel through the substrate to provide a path to release pressure and material caused by the microexplosion.

* * * * *